(12) United States Patent
Endou et al.

(10) Patent No.: US 6,197,806 B1
(45) Date of Patent: Mar. 6, 2001

(54) ELIMINATING AGENT FOR ACTIVATED OXYGEN AND FREE RADICALS

(75) Inventors: Hitoshi Endou, Kanagawa; Kazuharu Ienaga, Hyogo, both of (JP)

(73) Assignee: Nippon Zoki Pharmaceutical Co., Ltd., Osaka (JP)

( * ) Notice: Subject to any disclaimer, the term of this patent is extended or adjusted under 35 U.S.C. 154(b) by 0 days.

(21) Appl. No.: 08/769,008

(22) Filed: Dec. 18, 1996

(30) Foreign Application Priority Data

Dec. 20, 1995 (JP) .................................................. 7-349831

(51) Int. Cl.⁷ .................................................. A61K 31/445
(52) U.S. Cl. .............................................................. 514/389
(58) Field of Search ............................................. 514/389

(56) References Cited

U.S. PATENT DOCUMENTS

| | | |
|---|---|---|
| Re. 32,919 | 5/1989 | Sarnoff . |
| 3,818,031 | 6/1974 | Baerlocher et al. . |
| 4,096,130 | 6/1978 | Kraft et al. . |
| 4,647,574 | 3/1987 | Ienaga et al. . |
| 4,656,034 | 4/1987 | Sarnoff . |
| 4,658,830 | 4/1987 | Sarnoff . |
| 4,661,469 | 4/1987 | Sarnoff . |
| 4,683,240 | 7/1987 | Ienaga et al. . |
| 4,772,585 | 9/1988 | Sarnoff et al. . |
| 4,832,682 | 5/1989 | Sarnoff . |
| 4,985,453 | 1/1991 | Ishii et al. . |
| 5,002,930 | 3/1991 | Sarnoff et al. . |
| 5,078,680 | 1/1992 | Sarnoff . |
| 5,084,473 | 1/1992 | Mikami et al. . |
| 5,340,829 * | 8/1994 | Clark et al. ........................... 514/389 |
| 5,681,843 | 10/1997 | Kotani et al. . |

FOREIGN PATENT DOCUMENTS

| | | |
|---|---|---|
| 563 711 | 7/1975 | (CH) . |
| 2 214 448 | 10/1972 | (DE) . |
| 26 12 926 A1 | 10/1977 | (DE) . |
| 0 160 618 A1 | 11/1985 | (EP) . |
| 0 194 226 A1 | 9/1986 | (EP) . |
| 0 353 198 A1 | 1/1990 | (EP) . |
| 0 412 940 A2 | 2/1991 | (EP) . |
| 0 718 289 A1 | 6/1996 | (EP) . |
| 0 718 290 A1 | 6/1996 | (EP) . |
| 0721 944 | 7/1996 | (EP) . |
| 61/122275 | 6/1986 | (JP) . |
| 62/14 | 1/1987 | (JP) . |
| 63-166870 | 7/1988 | (JP) . |
| 64-56614 | 3/1989 | (JP) . |
| 2-40368 | 2/1990 | (JP) . |
| 2-167264 | 6/1990 | (JP) . |
| 2225485 | 9/1990 | (JP) . |
| 3-204874 | 9/1991 | (JP) . |
| 6-135968 | 5/1994 | (JP) . |
| 6-67827 | 8/1994 | (JP) . |
| 6-305964 | 11/1994 | (JP) . |
| 7-133264 | 5/1995 | (JP) . |
| 8-157473 | 6/1996 | (JP) . |
| WO 86/01110 | 2/1986 | (WO) . |
| WO 89/02890 | 4/1989 | (WO) . |

OTHER PUBLICATIONS

Kirsch, "Evidence for Free Radical Mechanisms of Brain Injury Resulting from Ischemia/Reperfusion–Induced Events," *Journal of Neurotrauma*, vol. 9, Supplement 1, 1992, pp. S157–S163.

Greenwald, "Therapeutic Usages Of Oxygen Radical Scavengers In Human Diseases: Myths and Realities," *Free Rad. Res. Comms.*, vols. 12–13, pp. 531–538, 1991.

Greenwald, "Superoxide Dismutase and Catalase As Therapeutic Agents For Human Diseases," *Free Radical Biology & Medicine*, vol. 8, pp. 201–209, 1990.

Rice–Evans et al., "Current Status Of Antioxidant Therapy," *Free Radical Biology & Medicine*, vol. 15, pp. 77–96, 1993.

Kanazu et al., "Aldehyde reductase is a major protein associated with 3–deoxyglucosone reductase activity in rat, pig and human livers," *Biochem J.*, 279, 903–906 (1991).

Flynn, "Aldehyde Reductases: Monomeric Nadph–Dependent Oxidoreductases With Multifunctional Potential," *Biochem. Pharmacol.*, vol. 31, No. 17, 2705–2712 (1982).

(List continued on next page.)

Primary Examiner—Zohreh Fay
(74) Attorney, Agent, or Firm—Hollander Law Firm, P.L.C.

(57) ABSTRACT

Hydantoin derivatives for eliminating free radicals and active oxygen which can be easily made into pharmaceutical preparations, show little, if any side effects, and are capable of being administered by the oral route. The pharmaceutical compositions for eliminating the active oxygen and the free radicals contain at least one hydantoin derivative represented by the following formula (I):

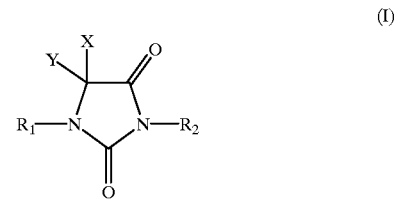

wherein each of $R_1$ and $R_2$, which may be the same or different, represents hydrogen, an alkyl group or a cycloalkyl group; and each of X and Y, which may be the same or different, represents hydrogen, a hydroxyl group, an alkyl group or an alkoxy group, or X and Y together represent an oxo group. The hydantoin derivatives which have an action of eliminating the active oxygen and the free radicals are, accordingly, useful as pharmaceutical agents for treating a variety of diseases in which active oxygen and free radicals are involved or play a detrimental role. Exemplary of the diseases which may be treated are myocardial infarction, reperfusion disturbance, autoimmune diseases, fibrosis, pulmonary diseases, dermatological diseases, arthropathy, side effects of anticancer agents, radiation diseases, septic shock, inflammatory diseases and cataracts.

21 Claims, 1 Drawing Sheet

OTHER PUBLICATIONS

"Pathologic Biochemistry and Clinics of Free Radicals, Inflammation and Antiinflammation," *Nippon Rinsho*, vol. 46, No. 10, pp. 93–97 (1988).

Yonezawa, et al., *Nippon Kagaku Zasshi*, 89, No. 8, pp. 62–64 (1968).

Patton, *J. Org. Chem.*, 32, No. 2, pp. 383–388 (1967).

Miyanoshita et al., "Inhibitory Effect Of Cyclic AMP On Phorbol Ester–Stimulated Production of Reactive Oxygen Metabolites In Rat Glomeruli", *Biochemical and Biophysical Research Communications*, vol. 165, No. 1, 1989, pp. 519–525.

K. Ogawva, et al., "Syntheses of substituted 2,4–dioxo–thienopyrimidin–1–acetic acids and their evaluation as aldose reductase inhibitors", *European Journal of Medicinal Chemistrychimica Therapeutica*, vol. 28, No. 10, 1993, pp. 769–781.

Morrison and Boyd, *Organic Chemistry*, Allyn and Bacon, Inc., Boston (1965), pp. 806, 808, 847–848.

Brownlee et al., "Aminoguanidine Prevents Diabetes–Induced Arterial Wall Protein Cross–Linking", *Science*, vol. 232, 1986, pp. 1629–32.

Ishii, et al., "Highly Selective Aldose Reductase Inhibitors", *J. Med. Chem.*, vol. 39, No. 9, 1996, pp. 1924–27.

Kato, et al., "Polyol Methabolism and Glycation in Diabetic Neuropathy", *Diabetes Front*, vol. 8, No. 4, 1997, pp. 510–511.

Kotani, et al., "Highly Selective Aldose Reductase Inhibitors. 3." *J. Med. Chem.*, vol. 40, No. 5, 1997, pp. 684–694.

Kotani, et al., "Highly Selective Aldose Reductase Inhibitors. II", *Chem. Pharm. Bull.*, vol. 45, No. 2, 1997, pp. 297–304.

Malamas, "Quinazolineacetic Acid and Related Analogues as Aldose Reductase Inhibitors" J. Med. Chem. (1991), 34,(4), 1492–503.

CA60:532c, abstract, 1990.

Grangier, "Reactivity of Nucleophilic Uracil Derivatives" *J. Heterocyclic Chem.* (1994), 31, (6), 1707–14, abstract.

* cited by examiner

ELIMINATING AGENT FOR ACTIVATED OXYGEN AND FREE RADICALS

FIELD OF THE INVENTION

The present invention relates to agents for eliminating active oxygen and free radicals containing a hydantoin derivative or a pharmaceutically acceptable salt thereof as an effective component. The reduction and elimination of free radicals and activated oxygen in living organisms and the treatment and prevention of a variety of diseases or conditions in which active oxygen and free radicals play a role are also provided by the present invention.

BACKGROUND OF THE INVENTION

Strong concern has been given in recent years to damage of molecules, membranes and tissues of living organisms by free radicals or by active oxygen and also to various diseases caused by such damage. Free radicals are chemical species having unpaired electrons and they are unstable and highly reactive. Activated oxygen species include superoxides, the hydroxyl radical, hydrogen peroxide and singlet oxygen. The superoxides and hydroxyl radical are radical species and, particularly, the hydroxyl radical has been known as a free radical having a very high reactivity. There are many target molecules in living organisms damaged by free radicals and active oxygen. Exemplary of such target molecules are lipids, nucleic acids, enzymes, proteins and sugars. Among these target molecules, highly unsaturated fatty acids, which are usually confined to lipids of cells, are especially apt to be attacked resulting in an oxidative degradation whereby lipid peroxides are produced. As a result of the production of lipid peroxides, cell membranes are damaged whereupon not only the membrane structure is destroyed but also enzymatic action and acceptor function of the proteins which are present and active there are greatly damaged. In addition, it has been known that the resulting lipid peroxides flow out from the topical region to blood causing a secondary pathology such as blood vessel pathology.

There have been many reports on the correlation of free radicals and active oxygen with diseases. The usefulness of substances having an ability to eliminate free radicals and active oxygen as pharmaceuticals has greatly attracted public attention. SOD (superoxide dismutase), which is a substance for eliminating the superoxides in living organisms, is a representative substance which eliminates free radicals and active oxygen and its development as a pharmaceutical agent is now under way. Therapeutic targets of SOD cover a wide variety of diseases including myocardial infarction, reperfusion disturbance, autoimmune diseases (such as collagen disease, Behçet disease and ulcerative colitis), fibrosis, pulmonary diseases (such as pulmonary edema and pulmonary fibrosis), dermatological diseases (such as burn injury, external wounds, keloid, hypersensitivity to sunlight and dermatitis), arthropathy, side effects of anticancer agents, radiation diseases, septic shock, inflammatory diseases and cataracts. See, for example, "Pathologic Biochemistry and Clinics of Free Radicals, Inflammation and Antiinflammation," *Nippon Rinsho*, volume 46, number 10, pages 93–97 (1988).

SOD is a protein preparation which problematically exhibits a short half life period in blood and minimal incorporation into cells. Therefore, various investigations on techniques for manufacturing preparations containing it are now being conducted. Consequently, there has been a demand for a novel agent for eliminating free radicals and active oxygen which can be easily made into pharmaceutical preparations and has little side effects.

Japanese Laid Open (Kokai) Nos. 61/122275 (published Jun. 10, 1986) and 62/14 (published Jan. 6, 1987) and their corresponding U.S. Pat. Nos. 4,647,574 and 4,683,240 each to Ienaga et al, respectively, disclose hydantoin derivatives and pharmaceutical compositions which contain them as having hypoglycemic, hypolipidemic and diuretic effects but do not disclose any eliminating action for free radicals or activated oxygen.

The present invention provides pharmaceutical compositions comprising pharmaceutically effective amounts of one or more hydantoin derivatives for eliminating free radicals and active oxygen which are readily produced, exhibit little or no side effects, and which may be administered orally. The compositions of the present invention may be used for the treatment and prevention of a variety of diseases or conditions in which active oxygen and free radicals play a role, such as myocardial infarction, reperfusion disturbance, autoimmune diseases, fibrosis, pulmonary diseases, dermatological diseases, arthropathy, side effects of anticancer agents, radiation diseases, septic shock, inflammatory diseases and cataracts.

SUMMARY OF THE INVENTION

The hydantoin derivatives and their pharmaceutically acceptable salts of the present invention exhibit substantial inhibitory action towards free radicals and active oxygen, such as superoxides, the hydroxyl radical, hydrogen peroxide and singlet oxygen, which can cause damage to molecules, membranes and tissues of living organisms. The derivatives and their salts at least substantially reduce or eliminate free radicals and active oxygen in living cells and organisms which can cause damage to target molecules such as lipids, highly unsaturated fatty acids, nuclei acids, enzymes, proteins, and sugars. The eliminating agents of the present invention include at least one hydantoin derivative represented by the general formula (I) or pharmaceutically acceptable salts of the derivatives represented by the general formula (I):

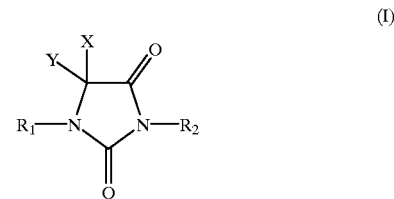

(I)

wherein each of $R_1$ and $R_2$, which may be the same or different, is hydrogen, an alkyl group or a cycloalkyl group; and each of X and Y, which may be the same or different, is hydrogen, a hydroxyl group, an allyl group or an alkoxy group, or X and Y together represent an oxo group.

The present invention also provides pharmaceutical compositions containing at least one of the derivatives of formula (I) or at least one salt thereof in a pharmaceutically acceptable amount with a pharmaceutically acceptable carrier or diluent.

The compounds and pharmaceutical compositions of the present invention may be used in pharmaceutically effective amounts to prevent damage to target molecules and cells caused by free radicals and activated oxygen in animals and humans. In accordance with the methods of the present invention, hydantoin derivatives and their pharmaceutically acceptable salts may be used to treat and prevent diseases in which active oxygen or free radicals are involved such as myocardial infarction, reperfusion disturbance, autoimmune diseases, fibrosis, pulmonary diseases, dermatological diseases, arthropathy, side effects of anticancer agents, radiation diseases, septic shock, inflammatory diseases and cataracts. The hydantoin derivatives may be administered orally to patients in need of treatment in effective, anti-oxidative amounts with little, if any side effects, low toxicity, and high safety.

DETAILED DESCRIPTION OF THE INVENTION

Figure 1:
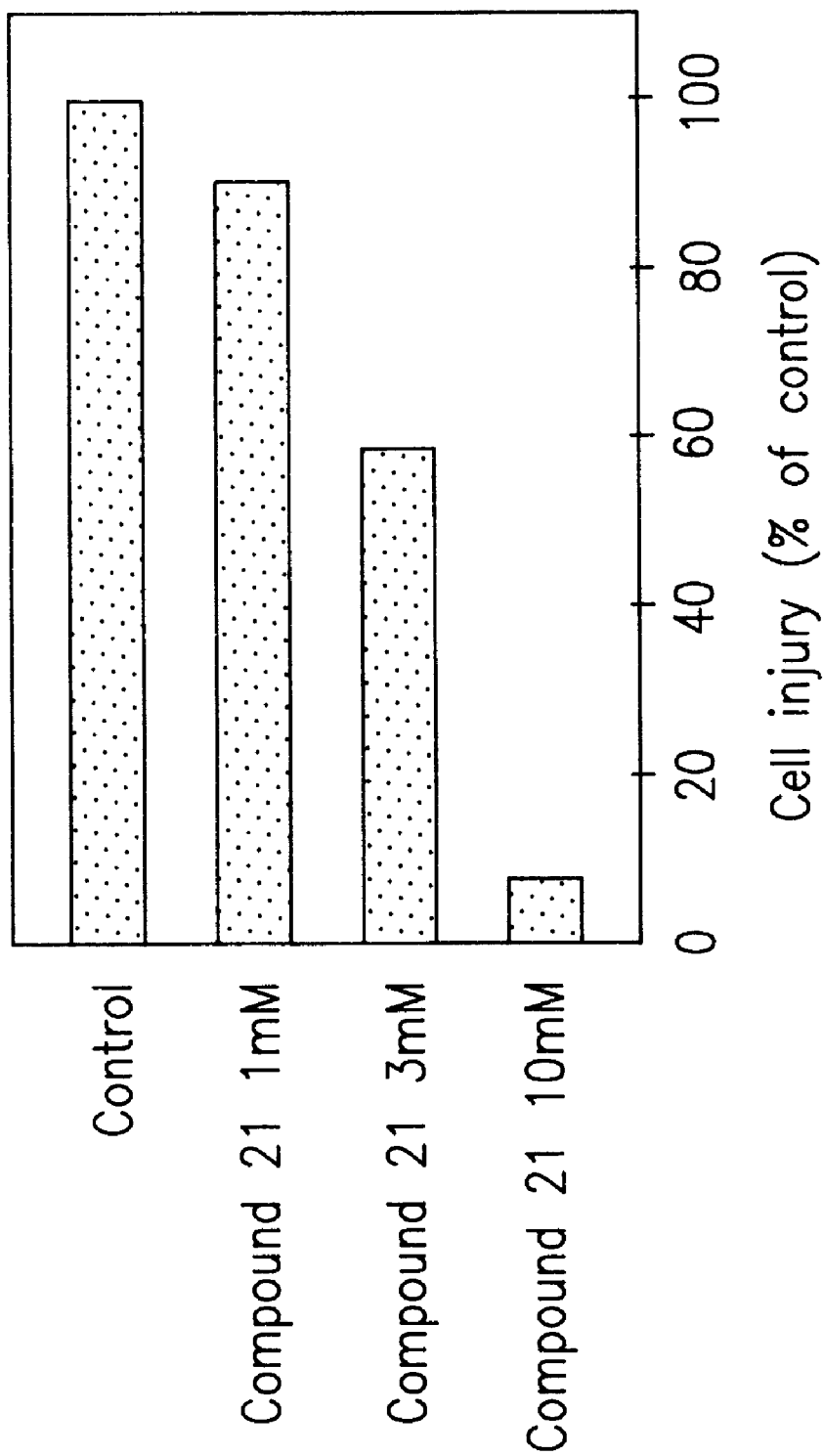
FIG. 1 shows an example of the results of inhibitory action of a compound of the present invention against damage of cells caused by hydroxyl radicals.

The effective component of the eliminating agent for active oxygen and free radicals in accordance with the present invention is a hydantoin derivative represented by the following formula (I) or a pharmaceutically acceptable salt thereof:

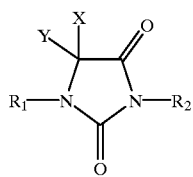

(I)

wherein each of $R_1$ and $R_2$, which may be the same or different, represents hydrogen, an alkyl group or a cycloalkyl group; and each of X and Y, which may be the same or different, represents hydrogen, a hydroxyl group, an alkyl group or an alkoxy group, or X and Y together represent an oxo group.

In the above mentioned formula (I), each of $R_1$ and $R_2$, which may be the same or different, represents hydrogen, an alkyl group, preferably a straight or branched alkyl group having 1 to 20 carbon atoms such as methyl, ethyl, propyl, isopropyl, butyl, isobutyl, sec-butyl, t-butyl, pentyl, isopentyl, neopentyl, t-pentyl, hexyl, dimethylbutyl, heptyl, octyl, nonyl, decyl or stearyl; or a cycloalkyl group, preferably a cycloalkyl group having 3 to 8 carbon atoms such as cyclopropyl, cyclobutyl, cyclopentyl, cyclohexyl, cycloheptyl or cyclooctyl.

Each of X and Y, which may be the same or different, represents hydrogen, a hydroxyl group, an alkyl group, preferably a straight or branched alkyl group having 1 to 3 carbon atoms such as methyl, ethyl, propyl, and isopropyl; or an alkoxy group, preferably a straight or branched alkoxy group having 1 to 5 carbon atoms such as methoxy, ethoxy, propoxy, isopropoxy, butoxy, isobutoxy, sec-butoxy, t-butoxy, pentoxy, isopentoxy, and neopentoxy; or X and Y together represent an oxo group.

Preferred compounds of the present invention are:

[Compound 1] Hydantoin
[Compound 2] 1-Methylhydantoin
[Compound 3] 3-Methylhydantoin
[Compound 4] 1-Ethylhydantoin
[Compound 5] 1-Propylhydantoin
[Compound 6] 1-Butylhydantoin
[Compound 7] 1-t-Butylhydantoin
[Compound 8] 1-Hexylhydantoin
[Compound 9] 1-(1,3-Dimethylbutyl)hydantoin
[Compound 10] 1-Decylhydantoin
[Compound 11] 1-Stearylhydantoin
[Compound 12] 1,3-Dimethylhydantoin
[Compound 13] 1,5-Dimethylhydantoin
[Compound 14] 3,5-Dimethylhydantoin
[Compound 15] 1-Cyclopentylhydantoin
[Compound 16] 1-Cyclohexylhydantoin
[Compound 17] 1-Cyclohexyl-3-methylhydantoin
[Compound 18] 3-Cyclohexylhydantoin
[Compound 19] 1,3-Dicyclohexylhydantoin
[Compound 20] 5-Hydroxyhydantoin
[Compound 21] 5-Hydroxy-1-methylhydantoin
[Compound 22] 5-Hydroxy-3-methylhydantoin
[Compound 23] 5-Hydroxy-1-ethylhydantoin
[Compound 24] 5-Hydroxy-1-propylhydantoin
[Compound 25] 5-Hydroxy-1-butylhydantoin
[Compound 26] 5-Hydroxy-1-t-butylhydantoin
[Compound 27] 5-Hydroxy-1-hexylhydantoin
[Compound 28] 5-Hydroxy-1-(1,3-dimethylbutyl)hydantoin
[Compound 29] 5-Hydroxy-1-decylhydantoin
[Compound 30] 5-Hydroxy-1-stearylhydantoin
[Compound 31] 5-Hydroxy-1-cyclopentylhydantoin
[Compound 32] 5-Hydroxy-1-cyclohexylhydantoin
[Compound 33] 5-Hydroxy-1-cyclohexyl-3-methylhydantoin
[Compound 34] 5-Hydroxy-1,3-dimethylhydantoin
[Compound 35] 5-Hydroxy-1,5-dimethylhydantoin
[Compound 36] 5-Hydroxy-3,5-dimethylhydantoin
[Compound 37] 5-Hydroxy-1,3-dicyclohexylhydantoin
[Compound 38] 5-Methoxyhydantoin
[Compound 39] 5-Methoxy-1-methylhydantoin
[Compound 40] 5-Methoxy-3-methylhydantoin
[Compound 41] 5-Methoxy-1-ethylhydantoin
[Compound 42] 5-Methoxy-1-propylhydantoin
[Compound 43] 5-Methoxy-1-butylhydantoin
[Compound 44] 5-Methoxy-1-cyclohexylhydantoin
[Compound 45] 5-Methoxy-3-cyclohexylhydantoin
[Compound 46] 5-Ethoxyhydantoin
[Compound 47] 5-Ethoxy-1-methylhydantoin
[Compound 48] 5-Ethoxy-3-methylhydantoin
[Compound 49] 5-Ethoxy-1-ethylhydantoin
[Compound 50] 5-Ethoxy-1-propylhydantoin
[Compound 51] 5-Ethoxy-1-butylhydantoin
[Compound 52] 5-Propoxyhydantoin
[Compound 53] 5-Propoxy-1-methylhydantoin
[Compound 54] 5-Propoxy-3-methylhydantoin
[Compound 55] 5-Propoxy-1-ethylhydantoin
[Compound 56] 5-Propoxy-1-propylhydantoin
[Compound 57] 5-Propoxy-1-butylhydantoin
[Compound 58] 5-Butoxyhydantoin
[Compound 59] 5-Butoxy-1-methylhydantoin
[Compound 60] 5-Butoxy-3-methylhydantoin
[Compound 61] 5-t-Butoxyhydantoin

[Compound 62] 5-t-Butoxy-1-methylhydantoin
[Compound 63] 5-t-Butoxy-3-butylhydantoin
[Compound 64] Imidazolidinetrione
[Compound 65] 1-Methylimidazolidinetrione
[Compound 66] 1-Ethylimidazolidinetrione
[Compound 67] 1-Butylimidazolidinetrione
[Compound 68] 1-Isobutylimidazolidinetrione
[Compound 69] 1-t-Butylimidazolidinetrione
[Compound 70] 1-Hexylimidazolidinetrione
[Compound 71] 1-(1,3-Dimethylbutyl)imidazolidinetrione
[Compound 72] 1-Decylimidazolidinetrione
[Compound 73] 1-Cyclopentylimidazolidinetrione
[Compound 74] 1-Cyclopentyl-3-ethylimidazolidinetrione
[Compound 75] 1-Cyclohexylimidazolidinetrione
[Compound 76] 1,3-Dimethylimidazolidinetrione
[Compound 77] 1,3-Dicyclohexylimidazolidinetrione The hydantoin derivatives of the present invention include the pharmaceutically acceptable salts of the compounds represented by the above given formula (I). Exemplary salts of the present invention are acid addition salts of the hydantoin derivatives of general formula (I) with hydrochloric acid, sulfuric acid, nitric acid, hydrobromic acid, phosphoric acid, perchloric acid, thiocyanic acid, boric acid, formic acid, acetic acid, haloacetic acid, propionic acid, glycolic acid, citric acid, tartaric acid, succinic acid, gluconic acid, lactic acid, malonic acid, fumaric acid, anthranilic acid, benzoic acid, cinnamic acid, p-toluenesulfonic acid, naphthalenesulfonic acid, or sulfanilic acid. Other salts of the present invention include salts of the hydantoin derivatives of general formula (I) with: a) an alkali metal such as sodium and potassium, b) an alkaline-earth metal such as calcium, magnesium and barium, and c) other metals such as aluminum and zinc.

The pharmaceutically acceptable salts may be manufactured, by conventional methods, starting from the hydantoin derivatives of the present invention in a free state or free form, or by conversion from one salt to another salt.

When there are steric isomers or stereoisomers such as cis-trans isomers, optical isomers, or conformational isomers for the compounds of the present invention, or when the compounds exist as hydrates or complexes, the present invention includes any and all of such isomers, hydrates and complexes.

The compounds of the present invention may be manufactured by conventional methods as disclosed, for example, in Japanese Laid Open (Kokai) Nos. 61/122275 (published Jun. 10, 1986) and 62/14 (published Jan. 6, 1987) and their corresponding U.S. Pat. Nos. 4,647,574 and 4,683,240 each to Ienaga et al, respectively. The disclosures of each of said Japanese publications and U.S. Pat. Nos. 4,647,574 and 4,683,240 are herein incorporated by reference in their entireties. For example, hydantoin derivatives of the present invention may be produced by methods as disclosed in U.S. Pat. No. 4,647,574 at column 2 line 39 to column 3 line 32. Thus, the hydantoin derivatives may be produced by first conventionally esterifying a glyoxylic acid. For example, a glyoxylic acid is reacted with an alcohol or 2-methoxyethanol, at room temperature or at a suitable temperature above room temperature or under reflux, for about several hours to about a day, with the produced water being removed, in the presence of an organic acid catalyst such as p-toluene-sulfonic acid or camphorsulfonic acid in an aprotic solvent such as benzene, toluene, xylene or carbon tetrachloride. Then the produced glyoxylic acid ester or an o-alkylglyoxylic acid ester (glyoxylic acid ester alcoholate) is, without being isolated or further purified, reacted at room temperature or heated under reflux for about 1 hour to about several days with, e.g., N-alkylurea, N-cycloalkylurea, N,N'dialkylurea or N,N'-dicycloalkylurea in an appropriate solvent such as water, acetic acid or alcohol, such as butanol or mixtures thereof, to give compounds of the present invention represented by the general formula (I).

The above-mentioned reaction can also be carried out with an α-ketocarbonic acid such as pyruvic acid as the starting material instead of a glyoxylic acid.

The compounds of the present invention wherein X or Y is an alkoxy group may be produced from a hydantoin derivative as prepared, e.g., by the process described above, by a conventional O-alkylation process. The hydantoin derivatives may be reacted with p-toluenesulfonyl chloride or mesyl chloride to introduce a removable residue into the hydroxy group at the 5-position, in the presence of an organic base such as a lower alkylamine or an alkali metal alkoxide in an appropriate solvent which does not inhibit the reaction. During or after the reaction, the resultant product is reacted with the alcohol corresponding to the X or Y substituent of the desired hydantoin derivative to give the compound of the present invention. This O-alkylation may be carried out at room temperature or at a suitable temperature above room temperature or under reflux, for about several hours to about several days.

The compounds of the present invention also include products from the N-alkylation of the hydantoin derivatives. The hydantoin derivative is reacted with a halogenated alkyl, a halogenated cycloalkyl, a dialkylsulfuric acid such as dimethylsulfonic acid, a p-toluenesulfonic acid alkyl ester or a p-toluenesulfonic acid cycloalkyl ester, in the presence of a base such as a lower alkyl amine, an alkali metal alkoxide or a hydroxyalkyl metal in an appropriate solvent which does not inhibit the reaction such as absolute alcohol, or dimethyl sulfoxide. The N-alkylation may be carried out at room temperature or at a suitable temperature above room temperature for about several hours to about several days.

When X and Y represent an oxo group, the hydantoin derivatives or imidazolidinetrione derivatives of the present invention may be produced by methods as disclosed in T. Yonezawa et al, *Nippon Kagaku Zasshi*, 89, No. 8, pp 62–64 (1968), Tad L. Patton, *J. Org. Chem.*, 32, No. 2, 383–388 (1967), and U.S. Pat. No. 4,683,240 at column 3 lines 27–49. For example, as disclosed in U.S. Pat. No. 4,683,240, oxalyl chloride and an N-substituted urea, such as an N-alkylurea, or N-cycloalkylurea may be stirred in an appropriate solvent such as tetrahydrofuran which does not inhibit the reaction in an ice-water bath or at room temperature. Alternatively, diethyl oxalate and the above-mentioned N-substituted urea may be stirred in an appropriate solvent which does not inhibit the reaction in the presence of an organic base such as an amine or alkali metal alkoxide at room temperature, if desired, by heating to higher temperatures to give the imidazolidinetrione derivatives of the present invention.

The compounds of the invention can also be prepared by conventional N-alkylation wherein unsubstituted, 1-alkylsubstituted or 1-cycloalkylsubstituted imidazolidinetrione is reacted with halogenated alkyl.

The compounds of the present invention prepared as described above may be purified by conventional methods such as distillation, chromatography and recrystallization. The compounds may be identified by means of, for example, elementary analysis, melting point measurement, infrared (IR), nuclear magnetic resonance (NMR), ultraviolet (UV), and mass spectroscopy (MS).

The compounds of the present invention, which include the hydantoin derivatives and their pharmaceutically acceptable salts and complexes, can be made into pharmaceutical preparations by combining one or more of the compounds with at least one pharmaceutically acceptable carrier or diluent. Any of the known methods for providing preparations, such as for oral administrations (e.g. tablets, capsules, powders, liquids, etc.) and for parenteral administrations (e.g. for subcutaneous, intravenous, intramuscular, intrarectal and intranasal administrations) may be used to produce the pharmaceutical compositions of the present invention. In preparing the preparations, the hydantoin derivatives of the present invention may be used in the form of their pharmaceutically acceptable salts. The compounds of the present invention may be used either solely or jointly in pharmaceutically effective amounts for treating animals or humans. The compounds of the invention can be used either solely or jointly together in pharmaceutically acceptable amounts with pharmaceutically effective amounts of other pharmaceutically active components in pharmaceutical compositions or preparations.

In the case of preparations for oral administration, one or more of the compounds of the present invention either alone or in combination with commonly-used pharmaceutically acceptable excipients in pharmaceutically acceptable amounts such as at least one suitable pharmaceutically acceptable additive or carrier (e.g. lactose, mannitol, corn starch, potato starch, potassium citrate, etc.) may be mixed with one or more pharmaceutically acceptable: (1) binders such as cellulose derivatives (e.g. crystalline cellulose, hydroxypropylcellulose, etc.), gum arabicum, corn starch, gelatin, etc., (2) disintegrating agents such as corn starch, potato starch, calcium carboxymethylcellulose, etc., (3) lubricating agents such as talc, magnesium stearate, etc. and (4) other pharmaceutically acceptable excipients including pharmaceutically acceptable bulking agents, moisturizing agents, buffers, preservatives, perfumes and the like to obtain tablets, diluted powders, granules or capsules.

In the case of injections, it is possible to prepare solutions or suspensions of one or more compounds of the present invention in pharmaceutically acceptable carriers such as an aqueous or nonaqueous solvent. Examples of solvents which may be used are distilled water for injection, physiological saline solution, Ringer's solution, plant oil, synthetic fatty acid glycerides, higher fatty acid esters, propylene glycol, etc.

It is also possible, depending upon the type of the disease, to prepare pharmaceutical preparations other than the above-mentioned ones which are suitable for therapy depending upon the state of the patient. Exemplary of other pharmaceutical preparations are syrups, suppositories, inhalations, aerosol preparations, collyriums, medicines for external use (e.g. ointments, gels, poultices), etc.

The preferred dosage of the compound of the present invention varies depending upon the subject to be administered (age, body weight, symptoms, etc. of the patient), form of the preparation, method for the administration, term for the administration, etc. To achieve the desired result, the compound may be usually administered by the oral route with a daily dose of 1–1,000 mg per day, preferably 5–600 mg per day, to common adults.

In the case of a parenteral administration such as by injection, the preferred dosage, may be from ⅓ to ⅒ of the above-mentioned oral dosages because of the effects of absorption, etc. in the oral route.

An example of a pharmaceutical formulation containing the compounds of the present invention as an effective component is given in Table 1, but is not intended to limit the scope of the invention:

TABLE 1

Tablet formulation

| Components | Amount per tablet |
|---|---|
| Compound of the present invention | 100 mg |
| Lactose | 35 mg |
| Crystalline cellulose | 5 mg |
| Hydroxypropylcellulose | 5 mg |
| Magnesium stearate | 5 mg |
| Total | 150 mg |

Preferred embodiments of the eliminating agent for active oxygen and free radicals containing the compound of the present invention represented by the above given formula (I) are:

(1) An eliminating agent for active oxygen and free radicals containing the compound represented by the formula (I) wherein one of X and Y represents a hydroxyl group.

(2) An agent according to the above subparagraph (1) wherein the other of X and Y represents hydrogen.

(3) An agent according to the above subparagraph (2) wherein one of $R_1$ and $R_2$ represents an alkyl group and the other represents hydrogen.

(4) An agent according to the above subparagraph (3) wherein $R_1$ represents an alkyl group.

(5) An agent according to the above subparagraph (4) wherein $R_1$ represents an alkyl group having 1 to 4 carbon atoms.

(6) An agent according to the above subparagraph (5) wherein $R_1$ represents methyl.

(7) An eliminating agent for active oxygen and free radicals containing the compound represented by the formula (I) wherein both of X and Y represent hydrogens.

(8) An agent according to the above subparagraph (7) wherein one of $R_1$ and $R_2$ represents an alkyl group and the other represents hydrogen.

(9) An agent according to the above subparagraph (8) wherein $R_1$ represents an alkyl group.

(10) An agent according to the above subparagraph (9) wherein $R_1$ represents an alkyl group having 1 to 4 carbon atoms.

(11) An agent according to the above subparagraph (10) wherein $R_1$ represents methyl.

(12) An agent according to the above subparagraph (1) wherein the other of X and Y represents an alkoxy group.

(13) An agent according to the above subparagraph (12) wherein $R_1$ represents an alkyl group and $R_2$ represents hydrogen.

(14) An agent according to the above subparagraph (13) wherein $R_1$ represents methyl.

(15) An agent according to the above subparagraph (1) wherein the other of X and Y represents an alkyl group.

(16) An agent according to the above subparagraph (15) wherein $R_1$ represents an alkyl group and $R_2$ represents hydrogen.

(17) An agent according to the above subparagraph (16) wherein $R_1$ represents methyl.

(18) An eliminating agent for active oxygen and free radicals containing the compound represented by the formula (I) wherein X and Y together represent an oxo group.

(19) An agent according to the above subparagraph (18) wherein $R_1$ represents an alkyl group and $R_2$ represents hydrogen.

(20) An agent according to the above subparagraph (19) wherein $R_1$ represents methyl.

(21) An eliminating agent for active oxygen and free radicals containing the compound represented by the formula (I) wherein one of X and Y represents an alkoxy group.

(22) An agent according to the above subparagraph (21) wherein $R_1$ represents an alkyl group and $R_2$ represents hydrogen.

(23) An agent according to the above subparagraph (22) wherein $R_1$ represents methyl.

(24) An eliminating agent for hydroxyl radicals containing the compound represented by the formula (I).

(25) An eliminating agent for hydroxyl radicals containing the compound defined in any of the above subparagraphs (1) to (23).

The present invention is illustrated by the following examples wherein all parts, percentages and ratios are by weight, all temperatures are in ° C., and all reactions are conducted at about atmospheric pressure unless indicated to the contrary:

EXAMPLE 1

Measurement of Ability for Eliminating Hydroxyl Radicals

Ability of the test substances for eliminating hydroxyl radicals was measured using an ESR spin trapping method which is frequently used for the detection of hydroxyl radicals. Generation of hydroxyl radicals was carried out using a Fenton's reaction in which hydroxyl radicals are generated by a reaction of divalent iron chelated with DTPA (diethylenediamine-pentaacetic acid) with hydrogen peroxide. DMPO (dimethylpyrroline N-oxide) promptly reacts with the hydroxyl radicals generated thereby and the resulting reaction product shows an ESR signal having four lines with a characteristic intensity ratio of 1:2:2:1. When a test substance having an eliminating action for hydroxyl radicals is present in this reaction system, the above characteristic signal is inhibited and, therefore, the ability for eliminating hydroxyl radicals can be measured using that signal inhibition as an index.

Thus, a solution of a mixture of 1 mM of ferrous sulfate and DTPA dissolved in 100 mM of a phosphate buffer (pH 7.8) was charged in a test tube. Then, 50 µl of a sample solution containing the test substance or hydantoin compound of the invention and 20 µl of 1 mM or 2 mM of DMPO were added. Finally, 75 µl of 1 mM of hydrogen peroxide solution was added to the resulting mixture to initiate the reaction. Hydrogen peroxide solution was prepared immediately before each of the experiments and the reaction was conducted at room temperature.

An ESR spectrum in this reaction system was measured by conventional means. Concentration ($IC_{50}$) of the test substance when the signal intensity for DMPO-OH was inhibited to an extent of 50% in the presence of the test substance or hydantoin derivative as compared to the signal intensity in the absence of the test substance was determined. In making the determination: 1) various concentrations of the test substance are tested, 2) the signal intensity is measured for each concentration, and 3) the concentration which results in 50% inhibition of the signal intensity compared to the signal intensity obtained in the absence of the test substance is the $IC_{50}$ concentration. The higher the $IC_{50}$ concentration of a test substance, the less is its ability to eliminate hydroxyl radicals because more of the test substance is required for the elimination. Dimethyl sulfoxide is a strong eliminating agent for hydroxyl radicals so it was used as a positive control for comparison. An example of the test results when 1 mM of DMPO was used is given in Table 2 below:

TABLE 2

Concentration of Test Substance at 50% Inhibition of Signal Intensity

| Test substance | $IC_{50}$ (M) |
| --- | --- |
| Dimethyl sulfoxide | $1.6 \times 10^{-4}$ |
| Compound 21 | $1.0 \times 10^{-3}$ |

EXAMPLE 2

Inhibitory Action Against Endothelial Cell Damage by Activated Leucocytes

Inhibitory action of the compounds of the present invention against damage of cells caused by hydroxyl radicals was measured using the following experimental system.

Endothelial cells of blood vessel obtained from bovine descending aorta by an enzymatic treatment were cultured in a 48 well plate using an MEM Eagle containing 15% of fetal calf serum. Then 3.7 KBq of $^{51}Cr$ (sodium chromate) was added to the endothelial cells in the confluent state and culturing was conducted for 18 hours whereby $^{51}Cr$ was incorporated into the endothelial cells. Chromium in the medium was washed out and the test substance or hydantoin derivative of the present invention, human leucocytes and phorbol ester (phorbol myristate acetate) were added thereto followed by culturing for six hours.

Radiation activity of chromium liberated into the medium from the endothelial cells was measured by a gamma-ray counter for: 1) the sample treated with the activated leucocytes in the presence of the test substance, 2) a sample without any treatments, and 3) a sample treated with Triton X-100. The sample without any treatments acts as a control to account for incorporated $^{51}Cr$ which is gradually released from the endothelial cells to the medium even without treatment with leucocytes. Thus, the sample without any treatments was not treated by leukocytes or a test substance. The sample treated with Triton X-100 is a control representing complete destruction of the cell (100% cell injury) and complete release of the $^{51}Cr$ into the medium. Triton X-100 is a polyethylene glycol p-isooctylphenyl ether or octoxynol produced by Rohm and Haas, Philadelphia, Pa. It is a detergent which dissolves endothelial cell membranes. So, all of the endothelial cells are damaged and all of the $^{51}Cr$ previously incorporated into the endothelial cells is released to the medium by the Triton X-100.

The degree of damage of the endothelial cells was calculated by the following formula wherein radiation activity of $^{51}Cr$ is used as the parameter for each sample:

(Degree of damage of endothelial cells) =

$$\frac{\text{(Sample treated with the activated leucocytes in the presence of the test substance)} - \text{(Sample without any treatments)}}{\text{(Sample treated with Triton X-100)} - \text{(Sample without any treatments)}}$$

The degree of damage of endothelial cells for the activated leucocytes only, i.e., in the absence of the test substance, was set to 100% as a control. An example of the results is given in FIG. 1.

As demonstrated by the test results of Examples 1 and 2, the compounds of the present invention exhibit an action of eliminating hydroxyl radicals. When the concentration of the added DMPO is changed in the pharmacological test of Example 1, the $IC_{50}$ of the compound of the present invention changes accordingly. Therefore, it is believed that the eliminating action of the compound of the present invention for hydroxyl radicals is a competitive antagonism to DMPO.

Consequently, the hydantoin derivatives of the present invention having an eliminating action to active oxygen and free radicals are useful as pharmaceuticals for treating a wide variety of diseases or conditions in which active oxygen or free radicals are involved including myocardial infarction, reperfusion disturbance, autoimmune diseases (such as collagen disease, Behçet disease and ulcerative colitis), fibrosis, pulmonary diseases (such as pulmonary edema and pulmonary fibrosis), dermatological diseases (such as burn injury, external wounds, keloid, hypersensitivity to sunlight and dermatitis), arthropathy, side effects of anticancer agents, radiation diseases, septic shock, inflammatory diseases and cataracts which have been known as diseases treated with SOD. Unlike dimethyl sulfoxide and the like having cytotoxic action, the compounds and pharmaceutical compositions of the present invention have very low toxicity and high safety and are capable of being administered by the oral route. Therefore, they can also be used to treat chronic diseases which need administration for long periods. The compounds may be used to substantially prevent or eliminate damage to target molecules, membranes, tissues, or cells of living organisms by a free radical or activated oxygen, and prevent the formation of peroxides such as lipid peroxides. Exemplary of target molecules which may be prevented from damage by free radicals or activated oxygen are lipids, unsaturated fatty acids, nucleic acids, enzymes, proteins, and sugars. As such, the hydantoin derivatives of the present invention and pharmaceutical compositions containing them are highly useful pharmaceuticals.

We claim:

1. A method for reducing free radicals or active oxygen in a patient in need of such reduction comprising administering to said patient a pharmaceutically effective amount of at least one hydantoin derivative or a pharmaceutically acceptable salt or complex of said derivative, said hydantoin derivative being represented by the formula (I):

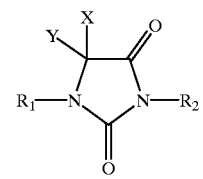

wherein each of $R_1$ and $R_2$, which may be the same or different, is hydrogen, an alkyl group or a cycloalkyl group; and each of X and Y, which may be the same or different, is hydrogen, a hydroxyl group, an alkyl group or an alkoxy group, or X and Y together is an oxo group, and wherein said patient is in need of treatment for a disease or a condition selected from the group consisting of myocardial infarction, reperfusion disturbance, autoimmune diseases, fibrosis, pulmonary diseases, dermatological diseases, arthropathy, side effects of anticancer agents, radiation diseases, septic shock and inflammatory diseases.

2. A method as claimed in claim 1 wherein said administration is to reduce hydroxyl radicals in a patient in need thereof.

3. A method as claimed in claim 1 wherein said administration is orally.

4. A method as claimed in claim 1 wherein said administration at least substantially prevents damage to target molecules by a free radical or activated oxygen, said target molecules being selected from the group consisting of lipids, unsaturated fatty acids, nucleic acids, enzymes, proteins, and sugars.

5. A method as claimed in claim 4 wherein said target molecules are lipids and said hydantoin derivative prevents the formation of lipid peroxides.

6. A method as claimed in claim 1 wherein said administration at least substantially prevents damage to cells by a free radical or activated oxygen.

7. A method as claimed in claim 6 wherein said administration at least substantially prevents damage to endothelial cells by hydroxyl radicals.

8. A method as claimed in claim 1 wherein one of X and Y is a hydroxyl group.

9. A method as claimed in claim 8 wherein the other of X and Y is hydrogen.

10. A method as claimed in claim 9 wherein one of $R_1$ and $R_2$ is an alkyl group and the other is hydrogen.

11. A method as claimed in claim 10 wherein $R_1$ is methyl.

12. A method as claimed in claim 1, wherein said patient is in need of treatment for a disease or a condition selected from the group consisting of myocardial infarction, reperfusion disturbance, autoimmune diseases, fibrosis, pulmonary diseases, dermatological diseases, arthropathy, septic shock, and inflammatory diseases.

13. A method for treating a disease or condition in which active oxygen or free radicals are involved comprising administering to a patient in need of treatment for said disease a pharmaceutically effective amount of at least one hydantoin derivative or a pharmaceutically acceptable salt or complex of said derivative, said hydantoin derivative being represented by the formula (I):

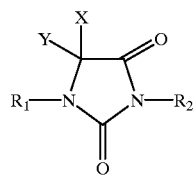

(I)

wherein each of $R_1$ and $R_2$, which may be the same or different, is hydrogen, an alkyl group or a cycloalkyl group; and each of X and Y, which may be the same or different, is hydrogen, a hydroxyl group, an alkyl group or an alkoxy group, or X and Y together is an oxo group, and wherein said disease or condition is selected from the group consisting of myocardial infarction, reperfusion disturbance, autoimmune diseases, fibrosis, pulmonary diseases, dermatological diseases, arthropathy, side effects of anticancer agents, radiation diseases, septic shock and inflammatory diseases.

14. A method as claimed in claim 13 wherein one of X and Y is a hydroxyl group.

15. A method as claimed in claim 14 wherein the other of X and Y is hydrogen.

16. A method as claimed in claim 15 wherein one of $R_1$ and $R_2$ is an alkyl group and the other is hydrogen.

17. A method as claimed in claim 16 wherein $R_1$ is methyl.

18. A method as claimed in claim 13, wherein said disease or condition is selected from the group consisting of myocardial infarction, reperfusion disturbance, autoimmune diseases, fibrosis, pulmonary diseases, dermatological diseases, arthropathy, septic shock, and inflammatory diseases.

19. A method as claimed in claim 18 wherein one of X and Y is a hydroxyl group.

20. A method as claimed in claim 19 wherein the other of X and Y is hydrogen.

21. A method as claimed in claim 20 wherein one of $R_1$ and $R_2$ is an alkyl group and the other is hydrogen.

* * * * *